United States Patent [19]

Bloom et al.

[11] Patent Number: 4,983,722

[45] Date of Patent: Jan. 8, 1991

[54] REMOVAL OF PROTEIN A FROM ANTIBODY PREPARATIONS

[75] Inventors: James W. Bloom, Richmond; Melvin F. Wong, San Francisco; Gautam Mitra, Kensington, all of Calif.

[73] Assignee: Miles Inc., Elkhart, Ind.

[21] Appl. No.: 204,054

[22] Filed: Jun. 8, 1988

[51] Int. Cl.$^5$ .......................... C07K 3/22; C07K 3/18
[52] U.S. Cl. .................... 530/387; 530/416; 530/417; 530/412; 530/413
[58] Field of Search ............... 530/387, 416, 417, 412, 530/413

[56] References Cited

U.S. PATENT DOCUMENTS 4,833,085  5/1989  Schaumann et al. .......... 435/240.27

OTHER PUBLICATIONS

Bonnerjea et al., 1986, Biol Technology 4:955–958.
Bensinger et al., 1984, J. of Biol. Resp. Modifier. 3:347–351.
Smith et al., 1983, Cleve Chin Q, 51:135–142.
Warner et al., 1986, J. of Immunol. Meth., 93:63–70.
Dertzbaugh et al., 1985, J. of Immunol. Meth., 83:169–177.
Schrezemeier et al., 1987, J. of Immunol. Meth., 105:133–137.
Martin, L. N., 1982, J. of Immunol. Meth., 50:319–329.
Manil et al., 1986, J. of Immunol. Meth., 90:25–37.
Langone, J. J., 1982, J. of Immunol. Meth., 55:277–296.

*Primary Examiner*—Margaret Moskowitz
*Assistant Examiner*—Keith C. Furman
*Attorney, Agent, or Firm*—James A. Giblin; Bertram Bradley

[57] ABSTRACT

Protein A is selectively isolated from an antibody—Protein A mixture by exposing the mixture to an anion exchange material under conditions sufficient to adsorb both components and then sequentially eluting the antibodies and protein A under conditions of increasing ionic strength. Resulting antibody preparations have less than about 15 ng of Protein A per mg of antibody.

5 Claims, 2 Drawing Sheets

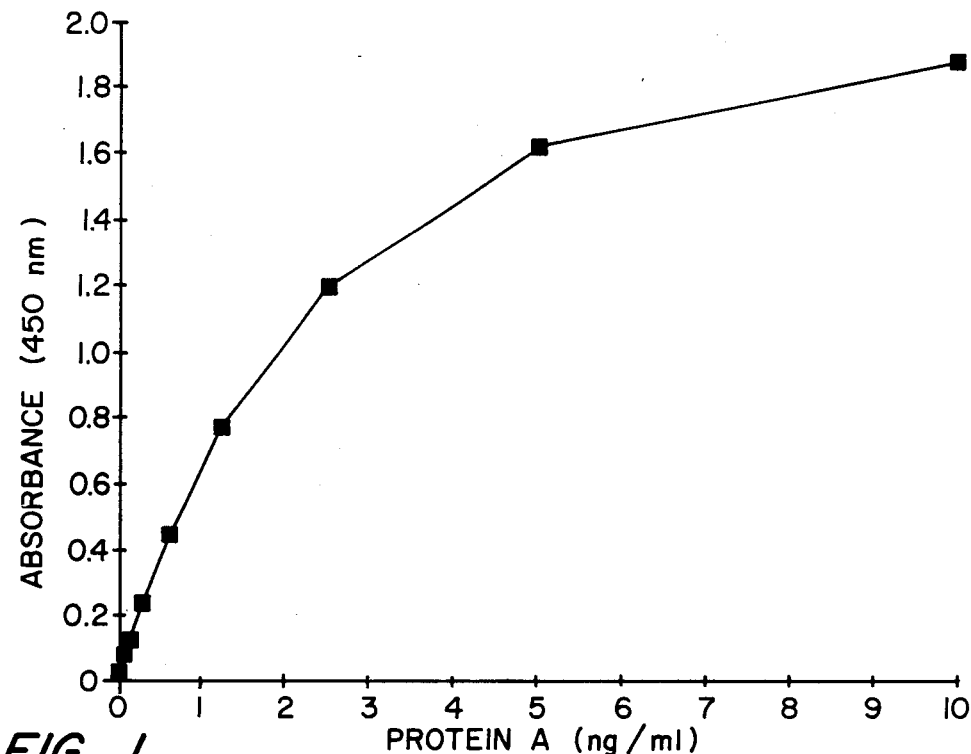
FIG._1.
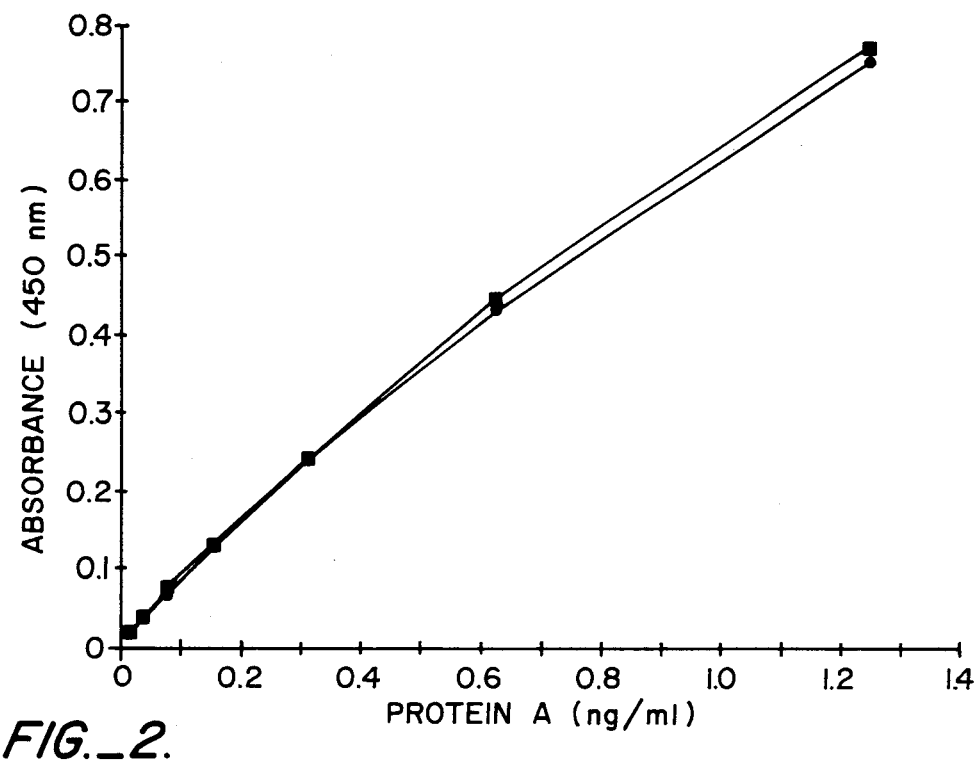
FIG._2.

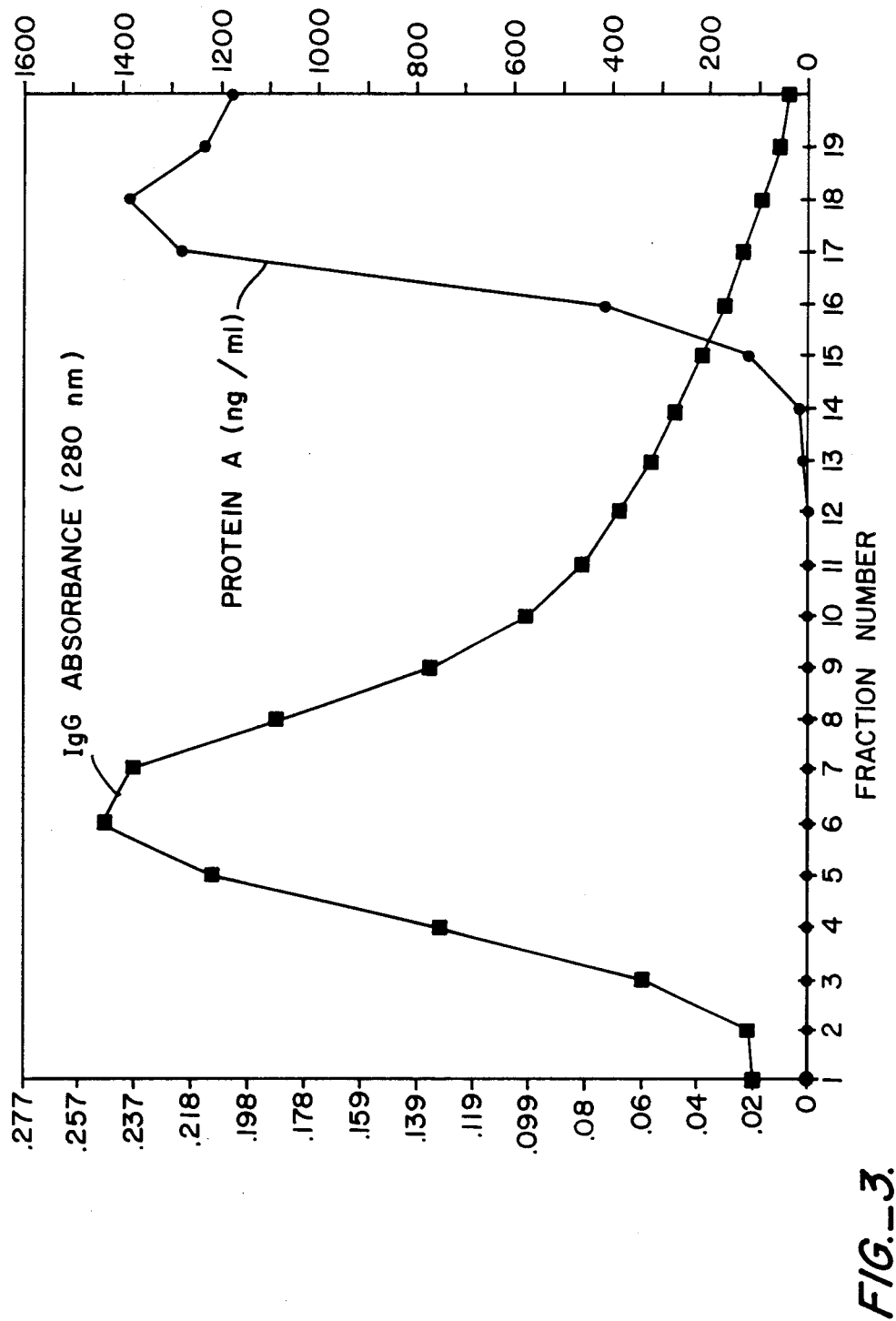
FIG._3.

REMOVAL OF PROTEIN A FROM ANTIBODY PREPARATIONS

BACKGROUND OF THE INVENTION

Field

This disclosure is concerned generally with the purification of biologically active proteins and specifically with the reduction of Protein A contamination in therapeutic antibody preparations.

Prior Art

Protein A is a well known substance obtained from *Staphylococcus aureus*, Cowan Strain I. It has a high degree of antibody specificity and the protein has long been used to complex with antibodies. Protein A is commonly used in an immobilized form by being attached to various water insoluble support materials. The immobilized protein A is then used to complex with soluble antibodies which are subsequently eluted from antibody—immobilized protein A complexes. Protein A chromatography is thus an excellent method for purifying ascites or tissue culture fluid derived monoclonal antibodies to homogeneity because of its simplicity and high degree of antibody specificity.

If the purified monoclonal antibodies are intended for therapeutic usage, however, a major safety concern is the possible presence of solubilized Protein A in the purified therapeutic product. Such solubilized Protein A is thought to result from the unintended detachment of Protein A from its support material during the purification process.

Numerous publications link Protein A with toxicity and mitogenicity in animal models and humans (see, for example, Bensinger et al., J. Biol. Resp. Modif. 3, 347, 1984; Messerschmidt et al., J. Biol. Resp. Modif. 3,325, 1984; Terman and Bertram, Eur. J. Cancer Clin. Oncol. 21, 1115; 1985; and Ventura et al., Hortobagyl. Cancer Treat Rep. 71,411, 1987).

Unfortunately, to date there have been no assay methods available to measure very low amounts of Protein A (i.e., less about than 15 pg of Protein A per mg of protein) that might be undesireably present in an antibody preparation intended for therapeutic use. Suprisingly, we found such an assay is now possible. Our assay led to a method of reducing Protein A contamination in antibody preparations to very low levels. The method thus permits the production of therapeutic antibody preparations using immobilized protein A while assuring a low degree of Protein A contamination. Details of our assay and purification methods are described below.

SUMMARY OF THE INVENTION

To evaluate the amount of Protein A column leakage, if any, into monoclonal antibodies purified with immobized Protein A we 1) developed a Protein A ELISA sensitive to the subnanogram range; 2) used the ELISA to determine Protein A levels in monoclonal antibodies purified by Protein A chromatography; and 3) devised a method to reduce solubilized Protein A found to be contaminating the antibody preparations. Our highly sensitive Protein A ELISA was made possible by using biotinylated anti-Protein A as the immunoassay label, thus allowing measurement of less than 15 ng of Protein A per mg of antibody. Our method of reducing the amount of Protein A in an antibody Protein A mixture comprises contacting the mixture with an anion exchange column under conditions sufficient to complex both components of the mixture onto an anion exchange material and then selectively eluting the components by carefully varying ionic strength under conditions sufficient to assure elution of an antibody preparation substantially free of Protein A (i.e. less than 15 ng of Protein A per mg of antibody). Preferably the Protein A content is less than about 1 ng per mg of antibody, and the purification step is accomplished by applying the mixture to an ion exchange column such as a DEAE Trisacryl M or DEAE Sepharose iron exchange material column and then eluting the antibody with a NaCl solution concentration gradient of about 0.025M to 0.25M as described below.

BRIEF DESCRIPTION OF THE FIGURES

FIG. 1 is a graph showing an ELISA for Protein A at concentrations ranging from 0.02 mg/ml to approximately 10 ng/ml.

FIG. 2 is a graph showing a redrawn portion of the standard curve from 0.02 ng/ml to 1.3 mg/ml.

FIG. 3 is a graph showing the column profile for the elution of both antibody and Protein A under conditions of increasing ionic strength.

SPECIFIC EMBODIMENTS

An enzyme labeled immunosorbent assay (ELISA) for low levels of Protein A was devised by biotinylating anti-Protein A IgG as follows:

Reagents

FTA Hemagglutination buffer (PBS) was obtained from BBL, Microbiology Systems (Cockeysville, Md). TMB (tetramethyl benzidine) Microwell Peroxidase Substrate and Peroxidase Substrate Solution B were obtained from Kirkegaard & Perry Labs, Inc. (Gaithersburg, Md). Rabbit anti-Protein A IgG (#45F-8806) and bovine albumin were obtained from Sigma (St. Louis, Mo). HRP-Streptavidin enzyme label was purchased from Zymed Laboratories, Inc. (San Francisco, Calif.) and Biotin-X-NHS biotin label compound from Calbiochem (La Jolla, Calif.). Natural Protein A AvidGel F immobilized protein was BioProbe International, Inc. (Tustin, Calif.). Recombinant Protein A was obtained from Repligen Corp. (Cambridge, Mass.). DEAE-Trisacryl M ion exchange material was obtained from LKB Instruments, Inc. (Gaithersburg, Md).

Methods

Rabbit anti-Protein A IgG was biotinylated according to the supplier's instructions. The procedure consisted of addition of 20 ul of 20 mg/ml Biotin-X-NHS to a 1 mg/ml antibody solution in 0.1 M bicarbonate buffer followed by gentle agitation for 1 hour at room temperature. Excess Biotin-X-NHS was then removed by dialysis against PBS buffer.

The concentration of the Protein A standard was determined using an extinction coefficient of 1.46 for a 1% solution at 275 nm (see Sjoqist et al., Eur. J. Biochem 29,572, 1972)

Our ELISA (Enzyme labeled immunosorbant assay) was performed as follows: Nunc Immuno Plate (#4-3945, InterLab, Thousand Oaks, CA) 96 well flat bottom ELISA plates were coated with 100 uL of 5 ug/ml anti-Protein A IgG diluted into 0.05M carbonate, pH 9.6 and incubated overnight at 5 C. The plates were then washed with wash buffer (PBS-0.05% Tween 20), blocked with 200 uL of wash buffer plus 1.5% BSA per well and incubated for one hour at 37 C. The plates were washed. Samples and the standard diluted in the wash buffer plus BSA were added in 100 uL aliquots to the plate and incubated for one hour at 37 C. Wells were set aside that contained only 100 uL of diluent to serve as blanks. The samples were discarded and the plates washed again with wash buffer. To each well 100 uL of biotinylated anti-Protein A IgG diluted in wash buffer plus BSA (approximately 1/16,000) was applied and incubated for 1 hr at 37 C. The antibody was discarded and the plates washed. Finally, 100 ul per well of Streptavidin-HRP was added and the plates were incubated for 1 hr at 37 C. The plates were washed and 100 uL of a 1:1 solution of TMB Microwell Peroxidase Substrate and Peroxidase Substrate Solution B was added per well and incubated for approximately 5 minutes at room temperature. 100 uL of 1N HCl was added to stop the reaction. The intensity of yellow color generated was proportional to the amount of Protein A present and was determined by measuring the absorbance at 450 nm on a Dynatech MR600 microtiter plate reader (Dynatech. Burlington, MA). The reading for each well was compensated for non-specific contributions by dividing by the absorbance at 570 nm. The average value of the blanks was subtracted to eliminate background. Experiments were done in duplicate on the same ELISA plate and average values utilized in the data analysis method.

ELISA RESULTS

ELISA sensitivity

Purified Protein A was tested in the ELISA at concentrations ranging from 0.02 ng/ml to 10 ng/ml. The results shown in FIG. 1 indicate saturation at approximately 10 ng/ml. The portion of the standard curve from 0.02 ng/ml to 1.3 ng/ml is redrawn in FIG. 2 with expanded scales and shows that the linear portion of the curve is approximately in the range of 0.05 ng/ml to 0.6 ng/ml.

ELISA validation

The Protein A ELISA was developed to quantitate Protein A in the presence of monoclonal antibodies. To determine whether the presence of a monoclonal antibody in stoichiometric excess would interfere with the assay the following experiment was undertaken. A 1 mg/ml solution of a monoclonal antibody purified to homogeneity by ion exchange chromatography was spiked with 10 ug/ml of purified Protein A. As a control and standard the ELISA dilution buffer was also spiked with 10 ug/ml Protein A. The mixtures were incubated for ½ hour at room temperature and then diluted to 20 ng/ml in the assay dilution buffer for assay. The results are shown in FIG. 2. The two curves are nearly superimposable. The results for the standard and spiked monoclonal antibody were 20 ng/ml and 18.3 ng/ml respectively. The difference of 9% can be attributed to experimental error. These results suggest that the presence of an excess amount of a monoclonal antibody does not significantly interfere with the ELISA.

Leakage of Protein A

The Protein A contamination levels of several monoclonal antibody preparations purified by Protein A chromatography were determined (Table I). Eluate pools 1a to 1d represent back-to-back 0.8 liter Protein A column runs with a 3 column volume purge of 0.2M glycine, pH 2.8 between runs. An initial Protein A level of approximately 300 ng/ml dropped to approximately to 40–100 ng/ml in subsequent runs.

Eluate pools 2 and 3 represent a 1.5 liter Protein A column containing a blend of the immobilized Protein A used to obtain Pool 1 eluates and new immobilized Protein A. Pool 2 eluate Protein A values are similar to Pool 1 but Pool 3 eluate values are considerably less. The amount of Protein A leakage seems to decrease with column usage.

TABLE 1

PROTEIN A LEAKAGE FROM IMMOBILIZED PROTEIN A COLUMNS USED TO PURIFY A MONOCLONAL ANTIBODY

| Eluate Pool # | Protein A(ng/ml) | Protein A/ Monoclonal(ng/mg) |
|---|---|---|
| 1a | 316.8 | 630 |
| 1b | 40.9 | 61 |
| 1c | 87.8 | 114 |
| 1d | 108.4 | 131 |
| 2a | 316.0 | 238 |
| 2b | 67.4 | 46 |
| 3a | 19.6 | 28 |
| 3b | 9.5 | 11 |

EXAMPLES

Monoclonal Antibody Purification

As measurable amounts of Protein A were present in monoclonal antibodies purified by immobilized Protein A, we looked for a method to reduce the Protein A contaminant levels. In an an initial experiment, a monoclonal antibody previously purified by Protein A chromatography was spiked with purified Protein A to a concentration of 0.59 ug Protein A per mg monoclonal antibody and subjected to DEAE chromatography. The column profile is shown in FIG. 3. Protein A eluted at a higher NaCl concentration than the IgG and good separation of the protein elution peaks was achieved.

To evaluate further the ability of DEAE chromatography to reduce Protein A contamination in a monoclonal antibody purified on a Protein A column, a Protein A eluate was chromatographed on DEAE (see Table 2).

TABLE 2

DEAE CHROMATOGRAPHY OF A MONOCLONAL ANTIBODY PURIFIED ON IMMOBILIZED PROTEIN A

| Fraction | IgG(mg/ml) | Protein A(ng/ml) | Protein A/ IgG(ng/mg) |
|---|---|---|---|
| Leading edge | 0.69 | 1.0 | 1.45 |
| Main peak | 3.13 | 7.8 | 2.49 |
| Trailing edge | 0.45 | 87.6 | 194.67 |

Significant separation of Protein A from the monoclonal was observed in confirmation of the spiking experiment. Details of a representative purification process are shown in the following example.

Monoclonal antibody purification: a IgG1 tissue culture fluid derived anti coagulant Factor VIII monoclonal antibody (designated C7F7) was purified in the following manner: 1) Tissue culture fluid is clarified by filtration, 2) Polyethylene glycol is added (17% w/v) to the supernatent solution and dissolved. Precipitate is separated and the solution is discarded. The precipitate is dissolved in 0.05 M tris(hydroxymethyl)aminomethane, 0.15 M sodium chloride, pH 8.00, to a volume of 2.5% of the original tissue culture fluid. Dissolved precipitate may be stored frozen at −20 C. or colder; 3) Fresh or thawed dissolved precipitate is clarified by centrifugation and/or filtration; 4) Solution is contacted with Protein A Avidgel F (R) (or equilivant immobilized Protein A) equilibrated with dissolving buffer and washed with same. C7F7 is removed by elution with 0.05 M sodium acetate, 0.15 M sodium chloride pH 4.00; 5). The eluate is diafiltered against not less than 6 volumes of DEAE quilibration buffer (0.025 M sodium chloride, 0.025 M tris(hydroxymethyl)aminomethane, pH 8.60); 6) The solution is contacted with DEAE Sepharose (R) or equilivant anion exchange resin (previously equilibrated) and washed with DEAE equilibration buffer. C7F7 is eluted with a sodium chloride gradient from 0.025 M to 0.25 M. Eluate is collected based on A280. The trailing edge is discarded. The trailing edge is defined as less than 20% of the maximum peak A280; 7) Diafilter solution against not less than 6 volumes of phosphate buffered saline (8.9 mM disodium phosphate, 0.7 mM monosodium phosphate, 1.6 mM monopotassium phosphate, 0.15 M sodium chloride). Using the above methods, the Protein A content of the antibody preparation was reduced to less than 15 ng/mg antibody (i.e. range of Protein A was from 0.9 to 14 ng/mg of antibody.

Protein A levels in several Protein A purified monoclonal antibody preparations further purified with DEAE chromatography were found to be in the range 0.9 to 14 ng/mg.

DISCUSSION

Numerous ELISAs have been developed for the detection of Protein A in the nanogram range of sensitivity (Maxim et al., J. Clin. Microbiol. 4,418, 1976; Langone et al., J. Immunol. Methods 18,281, 1977; Fey and Burkhard, J. Immunol. Methods 47, 99, 1981; Lofdahl et al., Proc. Nat. Acad. Sci., U.S.A., 80,697, 1983; Olsvik and Berdal, Acta Pathol. Microbiol. Immunol. Scand. Sect. B. Microbiol. 89, 289, 1981; Dertzbaugh et al., J. Immunol. Methods 83, 169, 1985; Considine et al., Bios. Rep. 6, 933, 1986; Warnes, et al., J. Immunol. Methods, 93, 63, 1986). As our application involves assaying Protein A in the presence of excess amounts of IgG, the assay had to be capable of detecting both free Protein A and Protein A complexed to the Fc region of IgG. Thus the antibodies used in the ELISA have to be specific for epitopes on the Protein A molecule. The majority of the published Protein A ELISA techniques are unsuitable for this application because they utilize the Fc binding ability of Protein A in the assay (Maxim, et al., 1976; Langone et al., 1977; Fey and Burkhard, 1981; Lofdahl, et al., 1983; Olsvik and Berdal, 1981; Considine, et al., 1986; Warnes, et al., 1986). We have developed an ELISA utilizing an anti-Protein A coating antibody and biotinylated anti-Protein A as the detection antibody. The biotinylated secondary antibody ELISA had an assay sensitivity approximately one hundred fold greater than a similar assay using an alkaline phosphatase labeled reagent (Dertzbaugh et al., 1985). In addition, with a sensitivity less than 0.1 ng/ml, the ELISA is five to ten fold more sensitive than the most sensitive Protein A system yet published (Warnes, et al., 1986). Replacement of the rabbit anti-Protein A-biotin with rabbit anti-Protein A followed by goat anti-rabbit IgG-biotin might improve the assay sensitivity even more (Warnes, et al., 1986).

Protein A contamination of an affinity column purified monoclonal antibody has been previously reported (Dertzbaugh et al., J. Immunol. Methods 83, 169, 1985) and the Protein A values appear to be similar to those reported here. The 2-fluoro-1-methyl pyridinium toluene-4-sulfonate (FMP) activated gel used to link Protein A in our studies is reported to be a more stable linkage than the cyanogen bromide-activated gel (Ngo, Bio/Technology 4, 134, 1986) used by Dertzbaugh, et al. The observations that the leakage rates of the two Protein A matrices are similar and that usage seems to reduce leakage, support the hypothesis that the majority of the Protein A that leached off the columns was noncovalently bond to the matrix (Dertzbaugh et al., J. Immunol. Methods, 1985).

DEAE chromatography was demonstrated to effectively reduce Protein A contaminant levels in preparations of a mouse monoclonal antibody. In the presence of excess rabbit or human IgG, Protein A has been shown to form complexes with the molecular formula of [IgG2ProteinA]or the dimeric structure [(IgG)2-ProteinA]2 (Balint et al., Cancer Res. 44, 734, 1984; Das et al., Anal. Biochem., 145, 27, 1985). These complexes could be separated from IgG by Sepharose CL-6B (Balint et al., Cancer Res. 44, 734, 1984) or by gel filtration HPLC. Model complexes formed by adding protein A to serum or to monomeric IgG have been reported to activate Fc-bearing leukocytes and the complement system to generate oxidant and anaphylatoxin activity in vitro (Balint et al., Cancer Res. 44, 734, 1984). A purification step, such as DEAE or gel filtration chromatography, designed to reduce contaminant Protein A levels would minimize the possibility of toxic effects in recipients of therapeutic monoclonal antibodies.

Given the above disclosure and examples, it is thought that numerous variations will occur to those skilled in the art. Accordingly, it is intended that the above examples should be construed as illustrative and that the scope of the invention disclosed herein should be limited only by the following claims.

We claim:

1. A method of reducing the amount of protein A from a mixture of antibodies and protein A to less than about 15 ng of protein A per mg of antibodies, the method comprising the steps of contacting the mixture with an anion exchange material under conditions sufficient to adsorb both the antibodies and the protein A and then sequentially eluting the antibodies and Protein A under conditions of increasing ionic strength.

2. The method of claim 1 wherein the conditions of increasing ionic strength comprise eluting the antibody and protein A with a NaCl solution having a concentration gradient of about 0.025 M to 0.25 M and the amount of protein A is reduced to less than about 1 ng per mg of antibodies.

3. The method of claim 1 wherein the anion exchange material comprises Diethylaminoethyl (DEAE) Trisacryl M or DEAE Sepharose anion exchange material.

4. The method of claim 1 wherein the antibody preparation comprises monoclonal antibodies to blood coagulation Factor VIII and the protein A content is less than about 15 ng per mg of antibodies.

5. The method of claim 4 wherein the conditions of increasing ionic strength comprise eluting the antibody and protein A with an NaCl solution having a concentration gradient of about 0.025 M to 0.25 M and the amount of protein A is reduced to less than about 1 ng per mg of antibody.

* * * * *